US012690962B2

(12) United States Patent
Humair et al.

(10) Patent No.: US 12,690,962 B2
(45) Date of Patent: Jul. 28, 2026

(54) SINGLE CONDUIT HEART VALVE WITH UNITARY LEAFLET AND SKIRT

(71) Applicant: Boston Scientific Limited, Hamilton (BM)

(72) Inventors: Arnaud Humair, Mont-sur-Rolle (CH); Yutit Wanakoht, Orges (CH)

(73) Assignee: Boston Scientific Limited, Hamilton (BM)

( * ) Notice: Subject to any disclaimer, the term of this patent is extended or adjusted under 35 U.S.C. 154(b) by 722 days.

(21) Appl. No.: 17/487,177

(22) Filed: Sep. 28, 2021

(65) Prior Publication Data

US 2022/0096713 A1 Mar. 31, 2022

Related U.S. Application Data

(60) Provisional application No. 63/085,756, filed on Sep. 30, 2020.

(51) Int. Cl.
| | |
|---|---|
| *A61F 2/24* | (2006.01) |
| *A61L 27/36* | (2006.01) |
| *A61L 27/50* | (2006.01) |

(52) U.S. Cl.
CPC ........ *A61F 2/2412* (2013.01); *A61L 27/3625* (2013.01); *A61F 2/2415* (2013.01); (Continued)

(58) Field of Classification Search
None
See application file for complete search history.

(56) References Cited

U.S. PATENT DOCUMENTS

| | | | |
|---|---|---|---|
| 6,730,118 B2 | 5/2004 | Spenser et al. | |
| 8,246,678 B2 | 8/2012 | Salahieh et al. | |

(Continued)

FOREIGN PATENT DOCUMENTS

| | | |
|---|---|---|
| CA | 2905544 | 9/2014 |
| CN | 111867518 | 10/2020 |

(Continued)

OTHER PUBLICATIONS

"International Search Report and Written Opinion," for PCT Application No. PCT/EP2021/076589 mailed Jan. 4, 2022 (12 pages).

(Continued)

*Primary Examiner* — Rebecca S Preston
(74) *Attorney, Agent, or Firm* — Pauly, DeVries Smith & Deffner LLC

(57) ABSTRACT

Embodiments herein relate to prosthetic heart valves constructed with animal tissue wherein the leaflets are unitary with the inner skirt. In an embodiment, an implantable heart valve assembly is included having a plurality of valve leaflets, an inner skirt, and a metal frame, wherein the plurality of valve leaflets and the inner skirt are formed of a continuous piece of animal tissue. In another embodiment, a method of making an implantable heart valve assembly is included, the method including placing a piece of pericardial tissue over a mold, cross-linking the pericardial tissue in place over the mold, removing the pericardial tissue from the mold, and attaching the pericardial tissue to a frame, wherein the pericardial tissue forms a seamless junction between a plurality of valve leaflets and an inner skirt. Other embodiments are also included herein.

20 Claims, 17 Drawing Sheets

(52) U.S. Cl.

CPC ..... *A61F 2/2418* (2013.01); *A61F 2220/0075*
(2013.01); *A61F 2250/0028* (2013.01); *A61F*
*2250/0069* (2013.01); *A61L 27/3641*
(2013.01); *A61L 27/507* (2013.01); *A61L*
*2430/20* (2013.01)

(56)   References Cited

U.S. PATENT DOCUMENTS

| | | | |
|---|---|---|---|
| 8,790,397 B2 | 7/2014 | Mathison | |
| 8,845,720 B2 | 9/2014 | Conklin | |
| 9,089,422 B2 | 7/2015 | Ryan et al. | |
| 9,226,826 B2 | 1/2016 | Rust | |
| 9,259,313 B2 | 2/2016 | Wheatley | |
| 9,492,273 B2 | 11/2016 | Wallace et al. | |
| 9,744,031 B2 | 8/2017 | Girard et al. | |
| 9,814,572 B2 | 11/2017 | Edelman et al. | |
| 9,848,981 B2 | 12/2017 | Suri et al. | |
| 9,895,221 B2 | 2/2018 | Vidlund | |
| 10,028,826 B2 | 7/2018 | Yohanan et al. | |
| 10,098,734 B2 | 10/2018 | Hoang | |
| 10,966,821 B2 | 4/2021 | Delaloye | |
| 11,730,587 B2 | 8/2023 | Delaloye | |
| 2003/0229394 A1* | 12/2003 | Ogle | A61L 27/3691 |
| | | | 623/2.14 |
| 2004/0024452 A1* | 2/2004 | Kruse | A61F 2/2415 |
| | | | 623/2.12 |
| 2005/0137682 A1* | 6/2005 | Justino | A61F 2/2418 |
| | | | 623/2.14 |
| 2007/0073392 A1* | 3/2007 | Heyninck-Jantz | |
| | | | B23K 26/0823 |
| | | | 623/2.14 |
| 2007/0233228 A1* | 10/2007 | Eberhardt | H01M 4/131 |
| | | | 623/1.13 |
| 2009/0030511 A1 | 1/2009 | Paniagua et al. | |
| 2011/0295363 A1* | 12/2011 | Girard | A61F 2/2412 |
| | | | 623/1.26 |
| 2012/0123529 A1 | 5/2012 | Levi et al. | |
| 2012/0226348 A1 | 9/2012 | Lane et al. | |
| 2013/0325111 A1 | 12/2013 | Campbell et al. | |
| 2014/0350668 A1 | 11/2014 | Delaloye et al. | |
| 2015/0032205 A1* | 1/2015 | Matheny | A61L 27/54 |
| | | | 623/2.15 |
| 2015/0100118 A1 | 4/2015 | Benton | |
| 2016/0030167 A1 | 2/2016 | Delaloye et al. | |
| 2016/0242904 A1 | 8/2016 | Braido et al. | |
| 2016/0324631 A1 | 11/2016 | Lane et al. | |
| 2017/0000603 A1 | 1/2017 | Conklin et al. | |
| 2017/0049566 A1 | 2/2017 | Zeng et al. | |
| 2017/0065411 A1 | 3/2017 | Grundeman et al. | |
| 2017/0231761 A1 | 8/2017 | Cohen-Tzemach et al. | |
| 2017/0348100 A1 | 12/2017 | Lane et al. | |
| 2018/0318074 A1 | 11/2018 | Yohanan et al. | |
| 2019/0117390 A1 | 4/2019 | Neethling et al. | |
| 2019/0201193 A1 | 7/2019 | Delaloye et al. | |
| 2019/0202140 A1 | 7/2019 | Pelled et al. | |
| 2019/0274828 A1 | 9/2019 | Delaloye | |
| 2019/0274832 A1 | 9/2019 | Delaloye | |
| 2019/0290426 A1 | 9/2019 | Maimon et al. | |
| 2019/0314151 A1 | 10/2019 | Biadillah et al. | |
| 2019/0321171 A1 | 10/2019 | Morriss et al. | |
| 2019/0336278 A1 | 11/2019 | Essinger et al. | |
| 2020/0008938 A1 | 1/2020 | Yohanan et al. | |
| 2020/0069415 A1 | 3/2020 | Bialas et al. | |
| 2020/0188095 A1 | 6/2020 | Liu | |
| 2020/0261223 A1 | 8/2020 | Quadri et al. | |
| 2021/0220124 A1 | 7/2021 | Delaloye | |

FOREIGN PATENT DOCUMENTS

| | | |
|---|---|---|
| EP | 3761908 | 1/2021 |
| JP | 2021516569 | 7/2021 |
| WO | 2009156471 | 12/2009 |
| WO | 2010037141 | 4/2010 |
| WO | 2014140230 | 9/2014 |
| WO | 2015169866 | 11/2015 |
| WO | 2016164209 | 10/2016 |
| WO | 2019170706 | 9/2019 |

OTHER PUBLICATIONS

"Response to Communication Pursuant to Rules 161(1) and 162 EPC," for European Patent Application No. 21786794.4 filed Nov. 15, 2023 (11 pages).

"Second Office Action," for Chinese Patent Application No. 201980017649.5 mailed Aug. 30, 2023 (11 pages) with English Summary.

"Communication Pursuant to Article 94(3) EPC," for European Patent Application No. 19710630.5 mailed May 29, 2024 (7 pages).

"Office Action," for Japanese Patent Application No. 2023-519729 mailed Jun. 11, 2024 (10 pages) with English translation.

"First Office Action," for Chinese Patent Application No. 201980017649.5 mailed Dec. 6, 2022 (16 pages) with English Translation.

"International Preliminary Report on Patentability," for PCT Application No. PCT/EP2019/055501 mailed Sep. 17, 2020 (8 pages).

"International Search Report and Written Opinion," for PCT Application No. PCT/EP2019/055501 mailed Jun. 13, 2019 (13 pages).

"Non-Final Office Action," for U.S. Appl. No. 16/293,909 mailed Aug. 17, 2020 (16 pages).

"Notice of Allowance," for U.S. Appl. No. 16/293,909 mailed Dec. 9, 2020 (5 pages).

"Office Action," for Japanese Patent Application No. 2020-546901 mailed Oct. 19, 2021 (8 pages) with English Translation.

"Response to Communication Pursuant to Rules 161(1) and 162 EPC," for European Patent Application No. 19710630.5 filed Apr. 22, 2021 (11 pages).

"Response to Non-Final Rejection," mailed on Aug. 17, 2020 for U.S. Appl. No. 16/293,909, submitted via EFS-Web on Oct. 13, 2020, 12 pages.

Falk, Volkmar "TAVI: Future Developments," Powerpoint presentation from the 4th Aortic Live Symposium Oct. 23-24, 2017 in Hamburg, Germany (74 pages).

Walther "ACURATE neo Aortic Bioprosthesis for IMplantation using the ACURATE neo TA Transapical Delivery System in Patiends with Severe Aortic Stenosis," Clinical Investigation Plan by Symetis S.A., Sep. 8, 2015 retrieved from URL <https://clinicaltrials.gov/ProvidedDocs/28/NCT02950428/Prot_000.pdf> on Mar. 26, 2019 (76 pages).

"Office Action," for JP Patent Application No. 2023-519729 mailed Jan. 16, 2024 (9 pages), withEnglish translation.

"International Preliminary Report on Patentability," for PCT Application No. PCT/EP2021/076589 mailed Apr. 13, 2023 (9 pages).

"Notice of Allowance," for U.S. Appl. No. 17/222,640 mailed May 10, 2023 (26 pages).

"Response to Communication Pursuant to Article 94(3) EPC," for European Patent Application No. 19710630.5 filed Sep. 26, 2024 (16 pages).

"Communication Pursuant to Article 94(3) EPC," for European Patent Application No. 19710630.5 mailed Feb. 26, 2025 (4 pages).

"Communication pursuant to Article 94(3)," for European Patent Application No. 21786794.4 mailed Jul. 7, 2025 (7 pages).

"Response to Communication pursuant to Article 94(3)," for European Patent Application No. 19710630.5 filed Jun. 26, 2025 (15 pages).

"Response to Communication pursuant to Article 94(3)," for European Patent Application No. 21786794.4 filed Nov. 5, 2025 (13 pages).

"Notice of Publication," for EP Patent Application No. 26174384.3 mailed May 13, 2026 (2 pages).

"Office Action," for CN Patent Application No. 202180065330.7 mailed Feb. 27, 2026, with English summary (14 pages).

* cited by examiner

Placing a piece of natural tissue over a mold 1790

Cross-linking the pericaridal tissue in place over the mold 1792

Removing the pericardial tissue from the mold 1794

Attaching the pericardial tissue to a frame 1796

SINGLE CONDUIT HEART VALVE WITH UNITARY LEAFLET AND SKIRT

This application claims the benefit of U.S. Provisional Application No. 63/085,756, filed Sep. 30, 2020, the content of which is herein incorporated by reference in its entirety.

FIELD

Embodiments herein relate to prosthetic heart valves constructed with animal tissue wherein the leaflets are unitary with the inner skirt.

BACKGROUND

Heart valve surgery can be used to repair or replace diseased heart valves. For example, heart valve replacement may be indicated when there is a narrowing of the native heart valve, commonly referred to as stenosis, or when the native valve leaks or regurgitates. The repair or replacement of diseased heart valves can include, for example, the introduction of a prosthetic heart valve that includes biological tissue heterologous to the patient (e.g., a heterograft or xenograft).

SUMMARY

Embodiments herein relate to prosthetic heart valves constructed with animal tissue wherein the leaflets are unitary with the inner skirt. In a first aspect, an implantable heart valve assembly is included having a plurality of valve leaflets, the plurality of valve leaflets can include an animal tissue, an inner skirt, the inner skirt can include an animal tissue, and a metal frame, wherein the plurality of valve leaflets and the inner skirt are formed of a continuous piece of animal tissue.

In a second aspect, in addition to one or more of the preceding or following aspects, or in the alternative to some aspects, the animal tissue has a thickness of 100 to 500 microns.

In a third aspect, in addition to one or more of the preceding or following aspects, or in the alternative to some aspects, the animal tissue exhibits a different degree of cross-linking in different areas of the implantable heart valve assembly.

In a fourth aspect, in addition to one or more of the preceding or following aspects, or in the alternative to some aspects, further can include: an outer skirt, the outer skirt can include an animal tissue.

In a fifth aspect, in addition to one or more of the preceding or following aspects, or in the alternative to some aspects, the plurality of valve leaflets, the inner skirt, and the outer skirt are formed of a continuous piece of animal tissue.

In a sixth aspect, in addition to one or more of the preceding or following aspects, or in the alternative to some aspects, the plurality of valve leaflets, the inner skirt, and the outer skirt are formed of a single piece of pericardium.

In a seventh aspect, in addition to one or more of the preceding or following aspects, or in the alternative to some aspects, the outer skirt wraps around an end of the metal frame and rests against an outside surface of the metal frame.

In an eighth aspect, in addition to one or more of the preceding or following aspects, or in the alternative to some aspects, the plurality of valve leaflets and the inner skirt are sutured to the metal frame.

In a ninth aspect, in addition to one or more of the preceding or following aspects, or in the alternative to some aspects, the inner skirt can include a longitudinal suture line.

In a tenth aspect, in addition to one or more of the preceding or following aspects, or in the alternative to some aspects, the inner skirt is seamless.

In an eleventh aspect, in addition to one or more of the preceding or following aspects, or in the alternative to some aspects, the plurality of valve leaflets can include: commissures, a nadir, and a reinforcing structure, wherein the reinforcing structure is positioned in the area of at least one of the commissures and the nadir.

In a twelfth aspect, in addition to one or more of the preceding or following aspects, or in the alternative to some aspects, the plurality of valve leaflets exhibits a curved bias from in situ cross-linking.

In a thirteenth aspect, in addition to one or more of the preceding or following aspects, or in the alternative to some aspects, the plurality of valve leaflets exhibits a symmetric pericardial fiber orientation.

In a fourteenth aspect, in addition to one or more of the preceding or following aspects, or in the alternative to some aspects, the plurality of valve leaflets exhibits an asymmetric pericardial fiber orientation.

In a fifteenth aspect, a method of making an implantable heart valve assembly is included, the method including placing a piece of pericardial tissue over a mold, cross-linking the pericardial tissue in place over the mold, removing the pericardial tissue from the mold, and attaching the pericardial tissue to a frame, wherein the pericardial tissue forms a seamless junction between a plurality of valve leaflets and an inner skirt.

In a sixteenth aspect, in addition to one or more of the preceding or following aspects, or in the alternative to some aspects, the method can further include cutting the pericardial tissue to form valve leaflet edges.

In a seventeenth aspect, in addition to one or more of the preceding or following aspects, or in the alternative to some aspects, the method can further include suturing the pericardial tissue in place on the mold.

In an eighteenth aspect, in addition to one or more of the preceding or following aspects, or in the alternative to some aspects, the method can further include wrapping an end of the pericardial tissue up and over an end of the frame to form an outer skirt.

In a nineteenth aspect, in addition to one or more of the preceding or following aspects, or in the alternative to some aspects, placing a piece of pericardial tissue over a mold further includes rolling a sheet of pericardial tissue around the mold and forming a line of sutures longitudinally along the mold to hold the pericardial tissue in place.

In a twentieth aspect, in addition to one or more of the preceding or following aspects, or in the alternative to some aspects, placing a piece of pericardial tissue over a mold further includes placing a non-planar piece of fresh pericardial tissue over the mold.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

The human body has four heart valves: a pulmonary valve, a tricuspid valve, an aortic valve and a mitral valve. The purpose of the heart valves is to allow blood to flow in a particular direction through the heart and from the heart into the major blood vessels connected to the heart, such as the aorta and pulmonary artery. As the heart muscle contracts and relaxes, the valves open and shut, letting blood flow into the ventricles and atria at alternate times.

Prosthetic valves designed to replace a valve in the human body frequently include two or more leaflets (commonly three) that are attached to a frame. Prosthetic valves can be configured to allow one-way flow through the valve, such as by separating the leaflets from each other to open the valve thereby allowing flow and joining together the leaflets (valve leaflet coaptation) to close the valve thereby blocking flow. In some cases, prosthetic valves can further include an inner skirt and/or an outer skirt to restrict the path of flow through the valve.

Various embodiments described herein provide a valve with a reduced number of seams between discrete pieces of tissue material providing enhanced simplicity and increased durability and strength. Various embodiments described herein also solve manufacturing difficulties of multiple component assembly.

In various embodiments herein, a single continuous piece of natural tissue is used for a number of valve components, such as the leaflets, the inner skirt, and the outer skirt (if an outer skirt is included with the valve). In some embodiments, the tissue material can be attached or coupled to the frame through a series of sutures. In various embodiments, the inner skirt 106 can be seamless. In various embodiments, the outer skirt can be seamless. In various embodiments, the leaflets, the inner skirt and/or the outer skirt can be seamless, such that they are all formed from a single, unitary piece of tissue, without suturing or otherwise attaching two or more pieces of tissue together.

Figure 1:
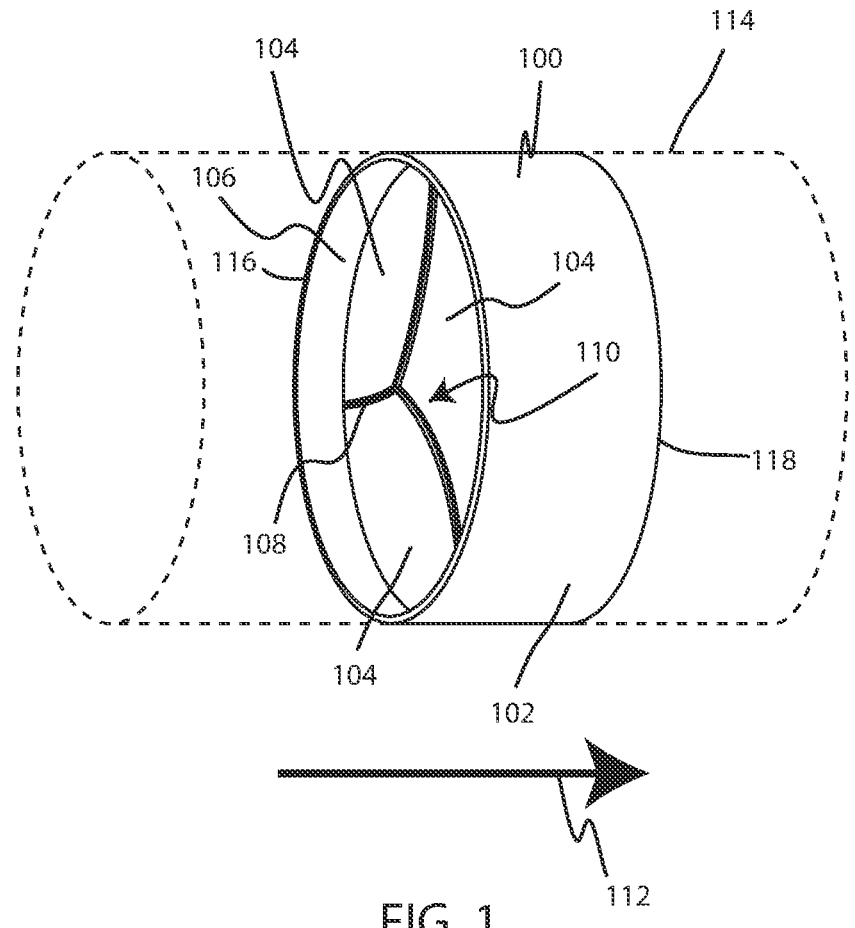
FIG. 1 is a schematic perspective view of a closed valve in a portion of an environment where it can be used in accordance with various embodiments herein.
Figure 2:
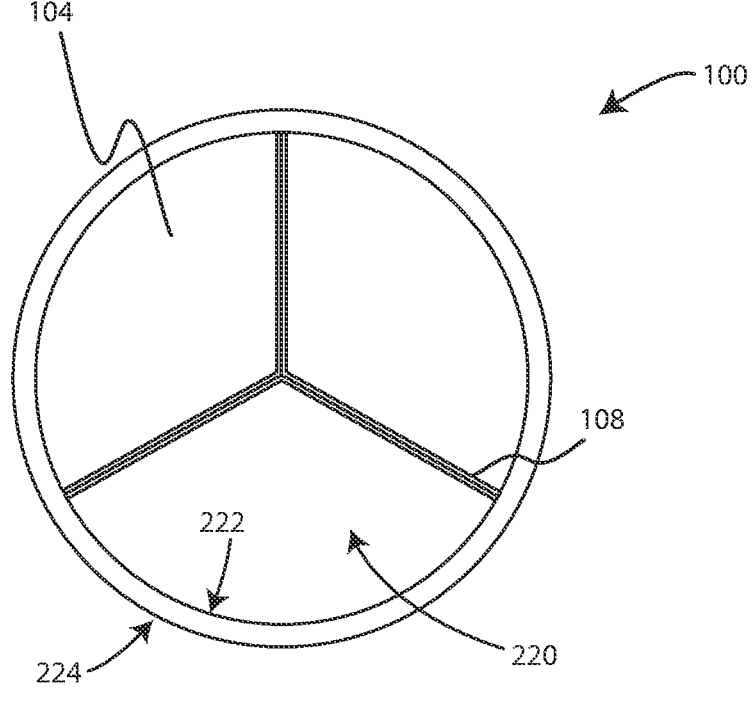
FIG. 2 is a schematic end view of a closed valve in a portion of an environment where it can be used in accordance with various embodiments herein.

FIG. 1 shows a schematic view of a closed valve 100 in a vessel 114, according to various embodiments. FIG. 2 shows an end view of the closed valve 100. It should be appreciated that the valve 100 can be any type of heart valve (e.g., a mitral valve, an aortic valve, etc.). In use, the valve 100 can be implanted (e.g., surgically or through transcatheter delivery) into a mammalian heart. The heart valve 100 can include an inlet 116. The heart valve 100 can also include an outlet 118. The valve 100 can be configured to allow one-way flow through the valve 100, such as depicted by arrow 112, which can represent blood flow during systole.

The valve 100 can include a frame 102 defining a central lumen 220 (see FIG. 2) which, in some embodiments, can be substantially cylindrical. The side of the frame 102 and other components facing the central lumen 220 can be referred to as the luminal surface 222 or luminal side. The opposite side of the frame 102 and other components (e.g., facing away from the central lumen 220) can be referred to as the abluminal surface 224 or abluminal side. In various embodiments, the frame 102 can have a substantially circular cross-section. However, in other embodiments, the frame 102 can have a non-circular, such as an oval or D-shaped, cross-section. In some embodiments, a non-circular frame 102 can be advantageously used to repair a mitral valve or another non-circular valve in the body.

The valve 100 can include a plurality of leaflets 104 disposed within the central lumen 220. Each leaflet 104 can include a free edge or coaptation edge 108 that is movable relative to the inner skirt 106 to coapt with the coaptation edges 108 of the other polymeric leaflets 104 along the coaptation region 110. In various embodiments, the plurality of leaflets 104 are formed with each other, such that the leaflets 104 are formed as a single unit. In some embodiments, a "root edge" can be an edge of the leaflet opposite from the coaptation edge 108, such as where the leaflets 104 joins the inner skirt 106. In various embodiments herein, the valve leaflets 104 can be integral (e.g., not existing as two separate pieces that are then joined together along a seam) with other structures such as an integral skirt (inner and/or outer), base structures, reinforcements, liners, leaflets or the like. In such circumstances the "root edge" is not a cut or otherwise divided edge, but rather is the location opposite the coaptation edge where the valve leaflet integrally meets those other structures.

The coaptation edges 108 of the leaflets 104 move into coaptation with one another in a closed position (FIGS. 1 and 2) to substantially restrict fluid from flowing past the valve 100 in a direction opposite to arrow 112. Specifically, the leaflets 104 can coapt to fill up or close the central lumen 220 of the valve 100 thereby impeding the flow of fluid opposite to direction of arrow 112.

Figure 3:
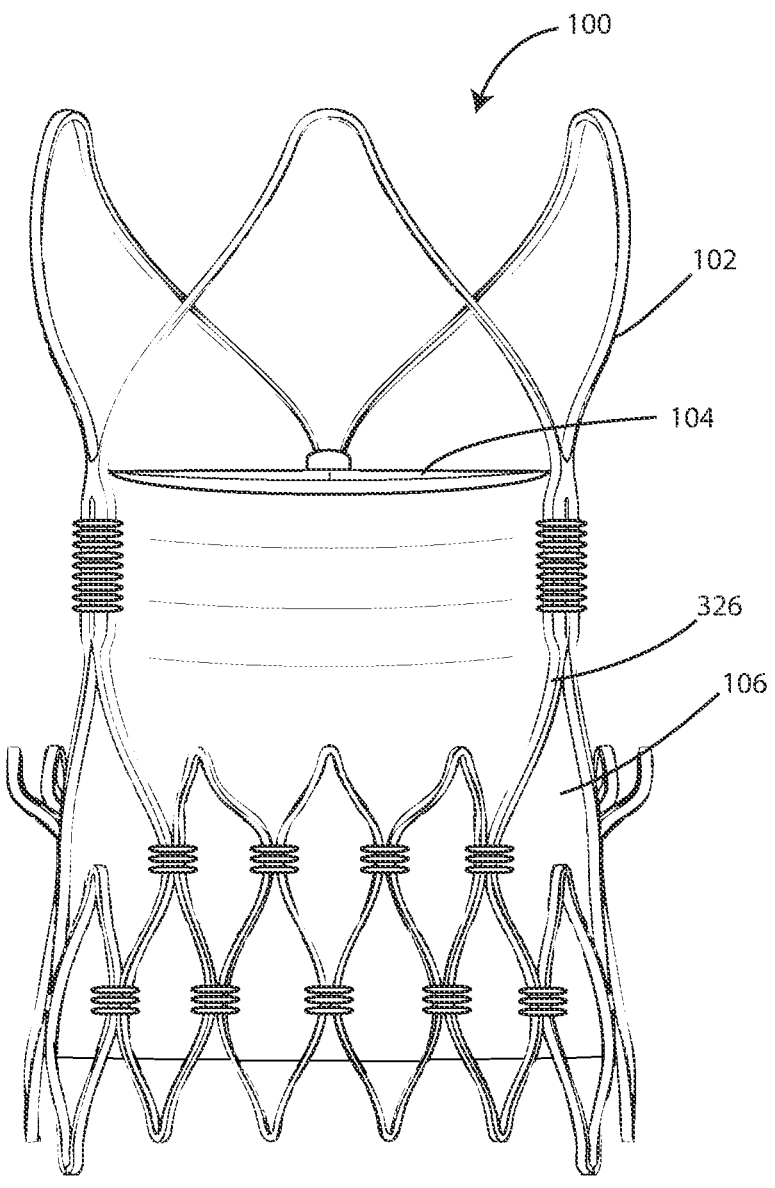
FIG. 3 is a perspective view of an implantable valve in accordance with various embodiments herein.

FIG. 3 shows a perspective view of an implantable valve 100, according to various embodiments. The valve 100 can include a frame 102, leaflets 104, and an inner skirt 106. In some embodiments, the valve 100 can include an outer skirt (not shown in FIG. 3). In some cases, the frame 102 can include a plurality of frame struts 326. However, frames lacking distinct struts are also contemplated herein.

The valve leaflets 104 can include a coaptation edge. The valve leaflets 104 can further include two connection portions. One connection portion can be disposed on either end of the coaptation edge such that the connection portions are contacting or adjacent to the frame 102. In some cases, the connections portions may also be referred to as commissures or commissural mounting tabs. The connection portions can be integral with the other portions of the valve leaflet 104 and other portions of the valve, such that the leaflets 104, inner skirt 106, and potential other portions are a single part.

In various embodiments, the implantable valve 100 can include an inner skirt 106. The inner skirt 106 can define a substantially tubular shape. The inner skirt 106 can be disposed on or otherwise supported by a luminal surface of the frame 102. The luminal surface of the frame 102 can be a surface of the frame 102 that defines the central lumen 220. The inner skirt 106 can direct fluid, such as blood, flowing through the valve 100. The inner skirt 106 can ensure the fluid flows through the central lumen 220 of the valve 100 and does not flow around the leaflets 104 when they are in a closed configuration.

In some embodiments, the implantable valve 100 can include an outer skirt (not shown). The outer skirt can define a substantially tubular shape. The outer skirt can be disposed on an abluminal surface of the frame 102. The abluminal surface of the frame 102 can be a surface of the frame 102 that is external to the central lumen 220. The outer skirt can be disposed between the frame 102 and a vessel 114 wall in order to prevent fluid, such as blood, flowing around the valve 100. The outer skirt can ensure the fluid flows through the valve 100 and does not flow around the valve 100, such as to ensure that the leaflets 104 can stop the flow of fluid when in a closed position.

In various embodiments, the plurality of valve leaflets 104 and the inner skirt 106 are formed of a continuous piece of animal-derived tissue. In various embodiments, the plurality of valve leaflets 104, the inner skirt 106, and the outer skirt are formed of a continuous piece of animal-derived tissue. In various embodiments, the plurality of valve leaflets, the inner skirt 106, and the outer skirt are formed of a single piece of pericardium.

Figure 4:
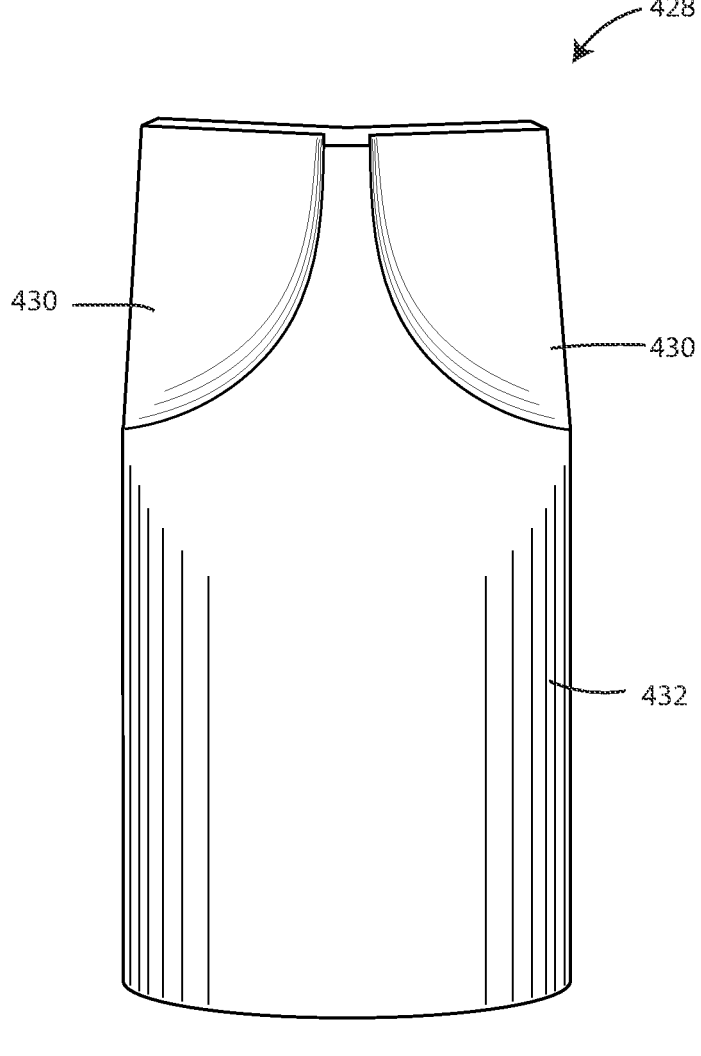
FIG. 4 is a perspective view of a mold in accordance with various embodiments herein.

In reference now to FIGS. 4-11 various steps in creating a valve 100 are shown. Referring now to FIG. 4, a perspective view of a mold 428 (or form or mandrel) is shown in accordance with various embodiments herein. The mold 428 includes indents 430. In some embodiments, the indents 430 can have a concave shape. The mold 428 also includes a body 432. In some embodiments, the body 432 can have a circular cross-section, such as to result in a valve 100 with a circular central lumen 220. However, other mold shapes are contemplated herein and it should be understood that different mold 428 shapes can result in different valve 100, such as a D-shaped mold 428 resulting in a D-shaped heart valve 100. In some embodiments, the body 432 of the mold can have an oval shaped cross-section.

The mold 428 can be used to form and/or shape portions of the heart valve 100, such as the leaflets 104, the inner skirt 106, and, in some embodiments, the outer skirt. The mold 428 can be used to form and/or shape a sheet of tissue into a desired configuration with leaflets 104 and an inner skirt 106. The mold 428 can be made of many different materials including a substantially rigid material such as a metal, polymer, ceramic, glass, composite, or the like. However, in some embodiments, the mold 428 may not be substantially rigid and can be capable of some degree of deformation.

A single continuous piece of tissue can be disposed on or around the mold as part of a process to transition the tissue from an original shape, such as a flat sheet, to a valve shape, where leaflets and an inner skirt are defined.

In some embodiments, the mold 428 can include indents 430. The indent 430 can align with portions of the tissue that will define the leaflet. Further, the mold body 432 can align with portions of the tissue that will define the inner skirt.

Figure 5:
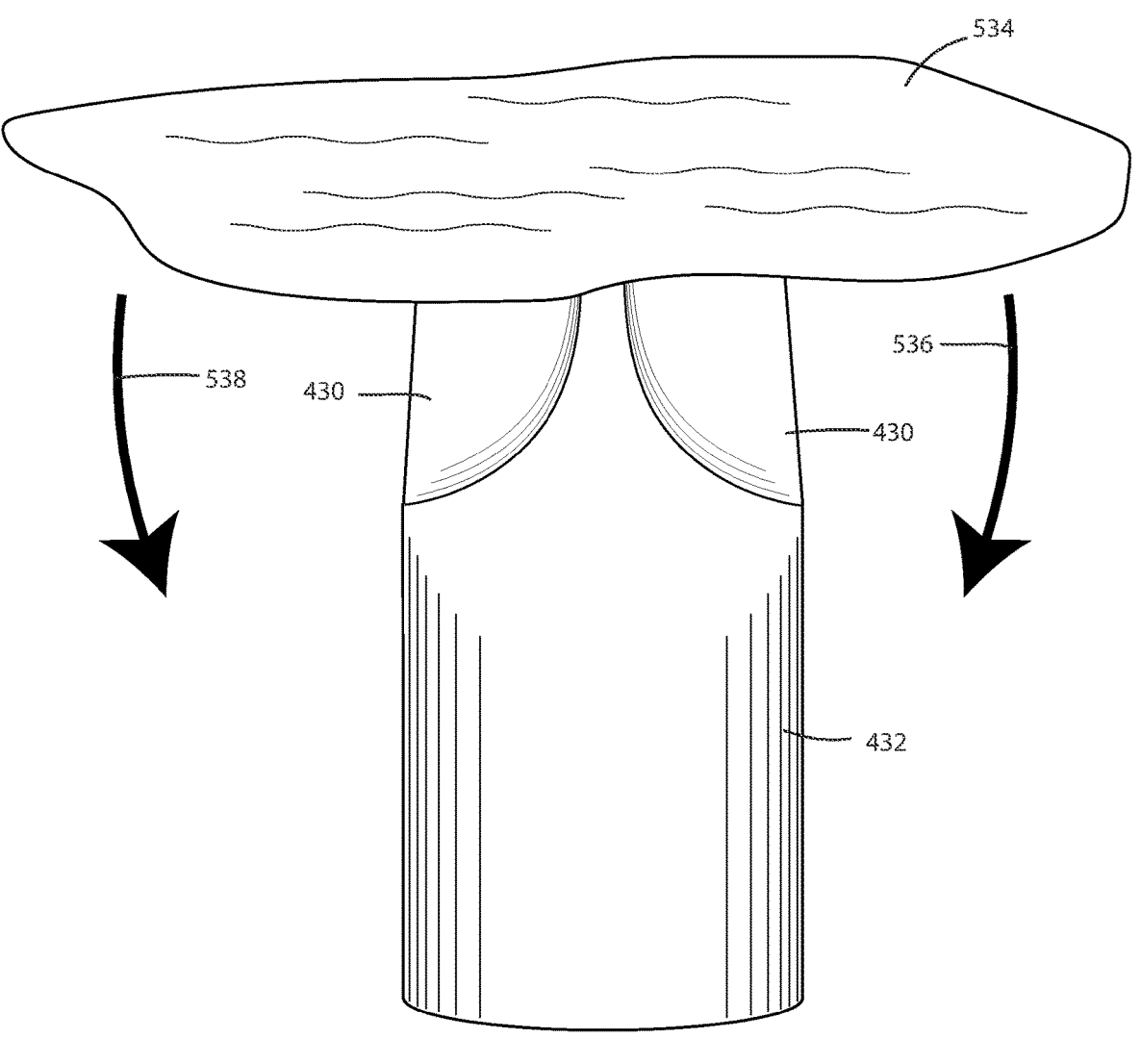
FIG. 5 is a perspective view of tissue being draped over a mold in accordance with various embodiments herein.

Referring now to FIG. 5, a perspective view of tissue 534 being draped over a mold 428 is shown in accordance with various embodiments herein. The mold 428 includes a plurality of indents 430, such as an equivalent number of indents 430 to the desired number of leaflets in the valve 100. In many embodiments, the mold 428 defines three indents 430 to result in a valve 100 with three leaflets 104. The mold 428 also includes a body 432, which can be sized and shaped to result in the desired size and shape of the inner skirt 106 and, in some embodiments, an outer skirt.

FIG. 5 specifically shows a single continuous sheet of tissue 534 being draped over the mold 428, such as portions of the tissue 534 moving in the direction of arrow 536 and arrow 538. The tissue 534 can be soft, flexible and/or malleable, such that the tissue 534 is able to take the shape defined by the outer portion of the mold 428 (including that defined by the indents and the body). The single continuous piece of tissue 534 can be used to form a plurality of leaflet 104, the inner skirt 106, and the outer skirt.

Figure 6:
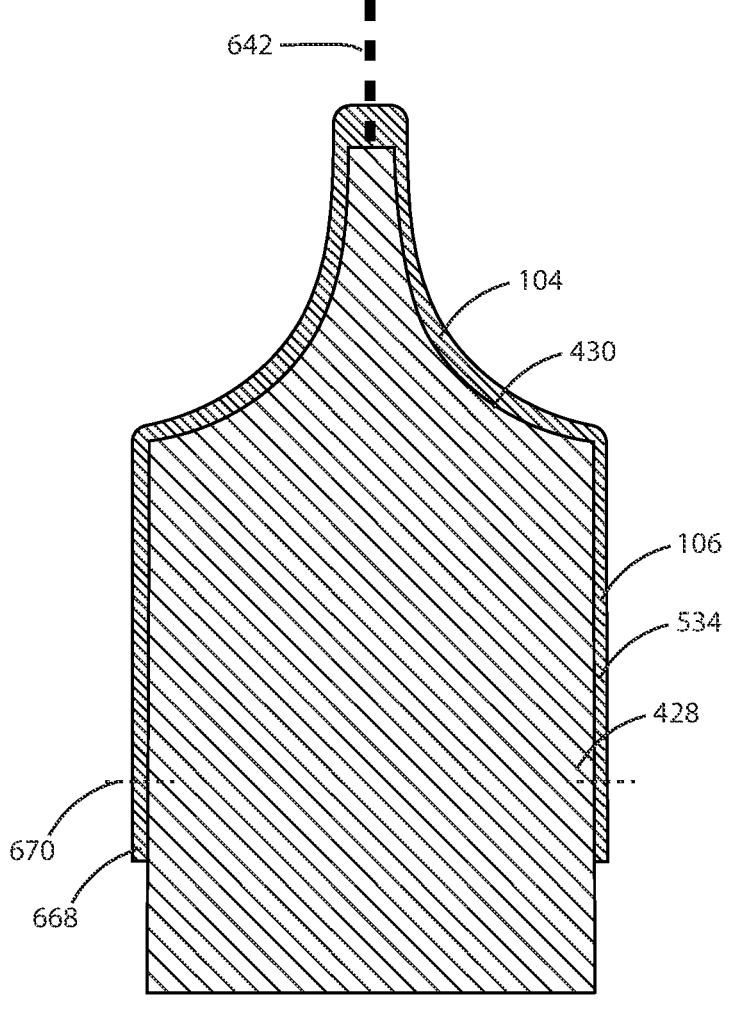
FIG. 6 is a cross-sectional view of tissue draped over a mold in accordance with various embodiments herein.

Referring now to FIG. 6, a cross-sectional view of the tissue 534 after it has been draped over the mold 428 is shown in accordance with various embodiments herein. It can be seen that the indents 430 align with the leaflet 104. The inner skirt 106 can be a portion of the tissue that is around the body 432 of the mold 428.

In some embodiments, the tissue 534 can be held on the mold 428 using vacuum pressure. In some embodiments, the tissue 534 can be held on the mold 428 using positive fluid pressure. In some embodiments, the tissue 534 can be held on the mold 428 using mechanical tension. In some embodiments, the tissue 534 can be held on the mold 428 using sutures.

In some embodiments, depending on how the tissue 534 is arranged on the mold 428, the tissue 534 can be cut, such as along cut line 642, to define coaptation edges and provide an opening through the tissue 534 that would allow blood to pass through the valve 100 and out the outlet 118.

In various embodiments, the valve 100 can include an outer skirt. The outer skirt 668 can extend past the inner skirt 106 on the mold 428, such as past line 670. Once the tissue 534 is positioned on a frame 102 and/or coupled to a frame 102, the outer skirt 668 can be flipped up or folded over line 670 (e.g. wrapping around a bottom edge of the frame) to form the outer skirt 668 on the frame 102. In various embodiments, the outer skirt wraps around an end of the metal frame 102 and rests against an outside surface of the metal frame 102.

Figure 7:
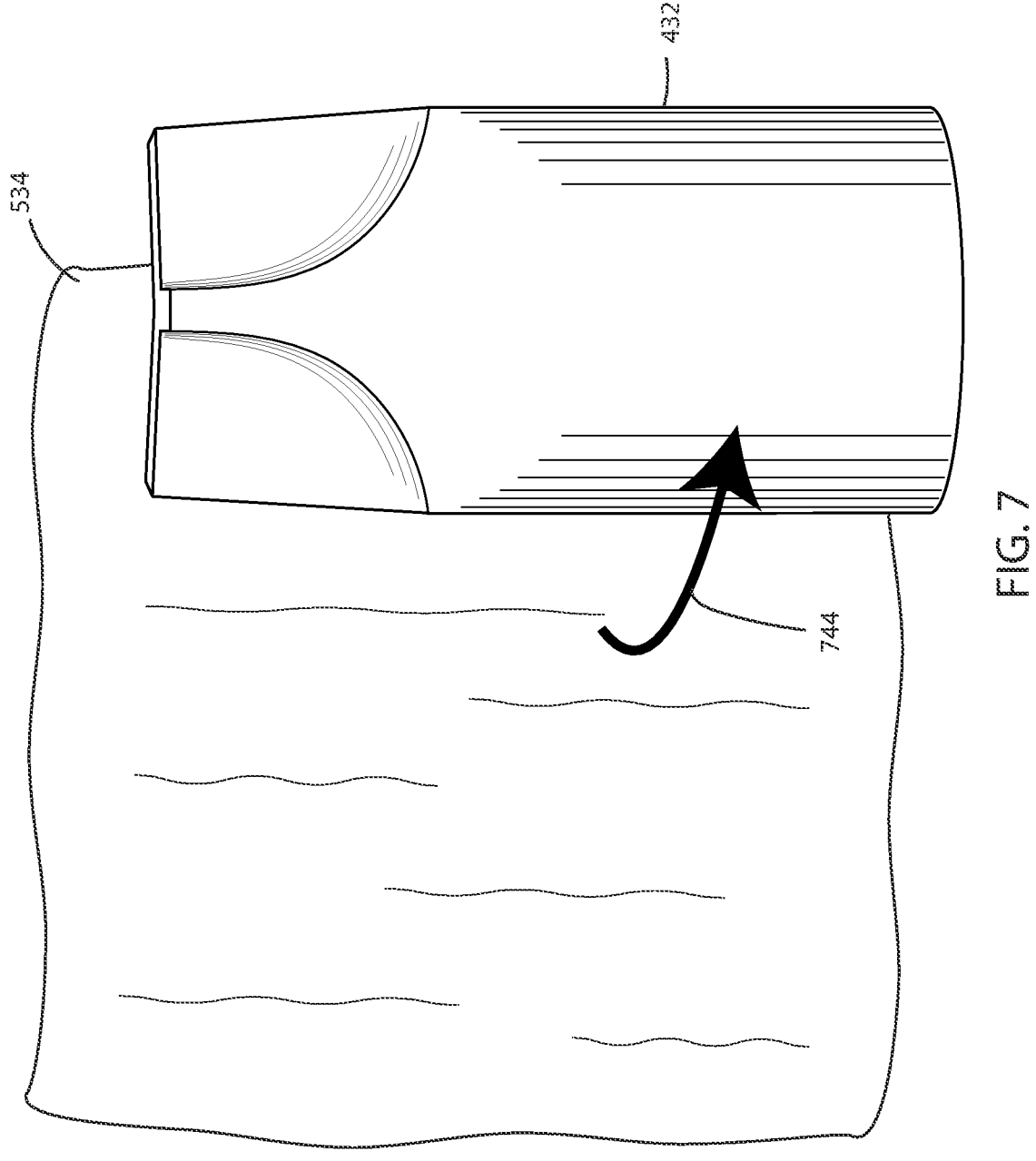
FIG. 7 is a perspective view of tissue being wrapped around a mold in accordance with various embodiments herein.

In contrast to FIG. 5, in some embodiments, the tissue 534 can be wrapped around a mold 428 laterally. Referring now to FIG. 7, a perspective view of tissue 534 being wrapped around a mold 428 is shown in accordance with various embodiments herein. Instead of draping the tissue 534 over the mold 428, the tissue 534 can be wrapped around the mold 428, such as indicated by arrow 744.

Figure 8:
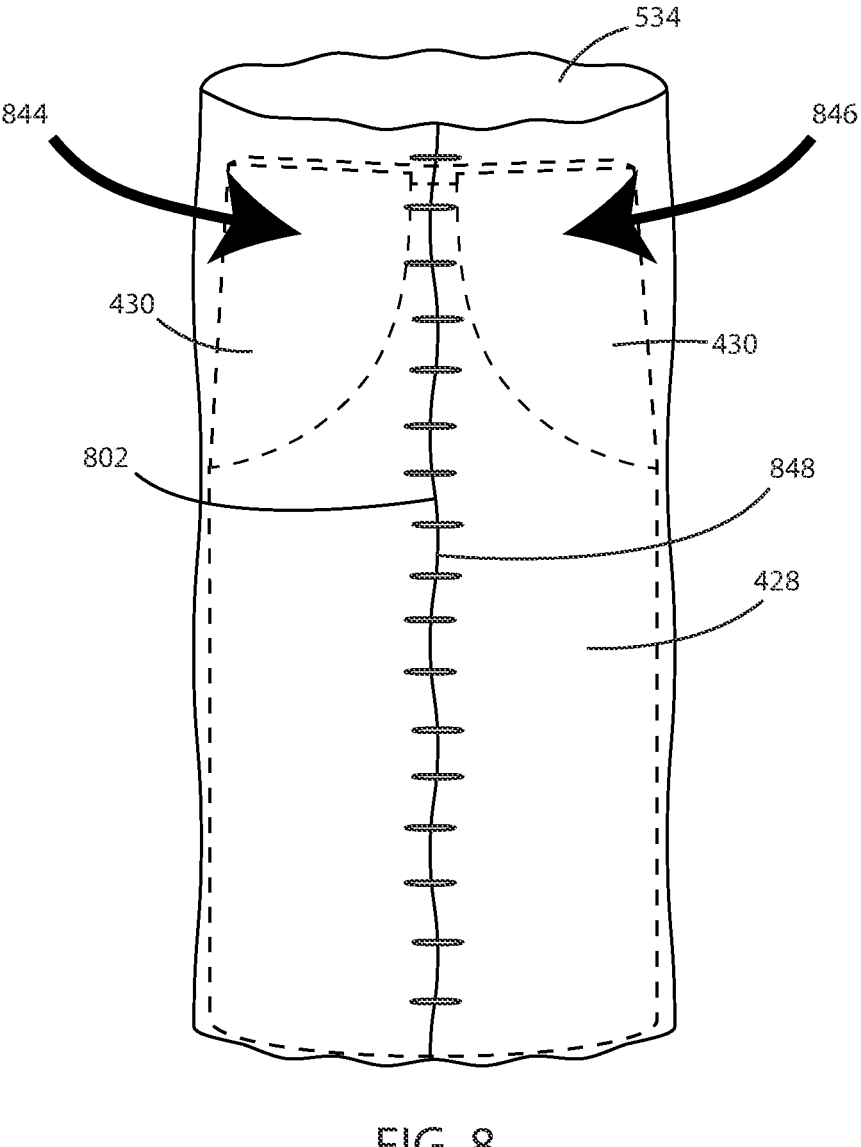
FIG. 8 is a perspective view of tissue being wrapped around a mold in accordance with various embodiments herein.

Referring now to FIG. 8, a perspective view of the tissue 534 being wrapped around a mold 428 is shown in accordance with various embodiments herein. Two ends of the tissue 534 can be joined with a suture line 848, such as a single longitudinal suture line. Thus, where the two ends meet a seam 802 is formed. However, the seam 802 extends along the longitudinal axis and does not divide the inner skirt area from the leaflets and/or does not divide the inner skirt area from an outer skirt area. The suture line 848 can include a plurality of sutures to attach the two ends of the same piece of tissue 534 together. The suture line 848 can have varying densities of sutures. Sutures can also be used to pull the tissue 534 tightly to the mold 428, such that the tissue 534 takes the same shape as the outer surface of the mold 428. Then, portions of the tissue 534 can be pushed inward in the direction of arrows 844 and 846 so that the tissue 534 conforms with the shape of indents 430.

Figure 9:
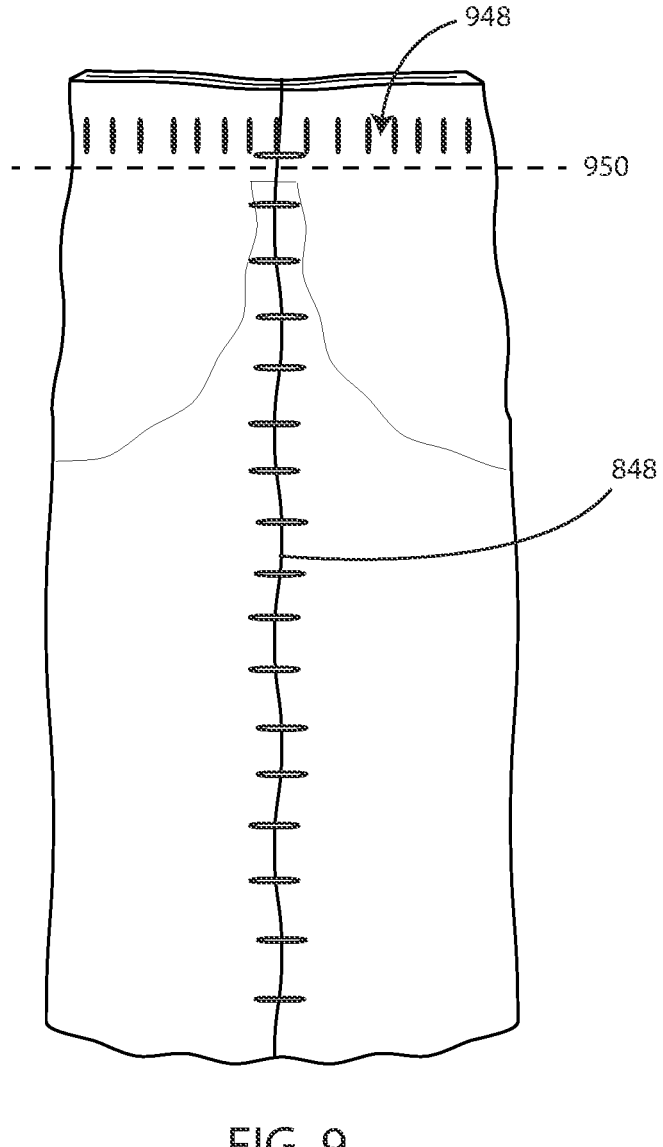
FIG. 9 is a perspective view of tissue wrapped around a mold in accordance with various embodiments herein.

Referring now to FIG. 9, a perspective view of the tissue 534 wrapped around a mold 428 is shown in accordance with various embodiments herein. FIG. 9 includes features as shown in FIG. 8, but further shows a second suture line 946, which can be included in some embodiments. The second suture line 946 can be used to hold the tissue 534 in place and against the mold surface, similar to suture line 848. In some embodiments, the second suture line 946 can be removed from the remainder of the tissue 534, such as by cutting along line 950. As such, the second suture line 946 does not become a part of the finished valve. Rather, the second suture line 946 is only used in the process of forming the valve. Cutting along line 950 can also create an opening through the tissue 534, such as to form the outlet 118 of the central lumen 220.

Figure 10:
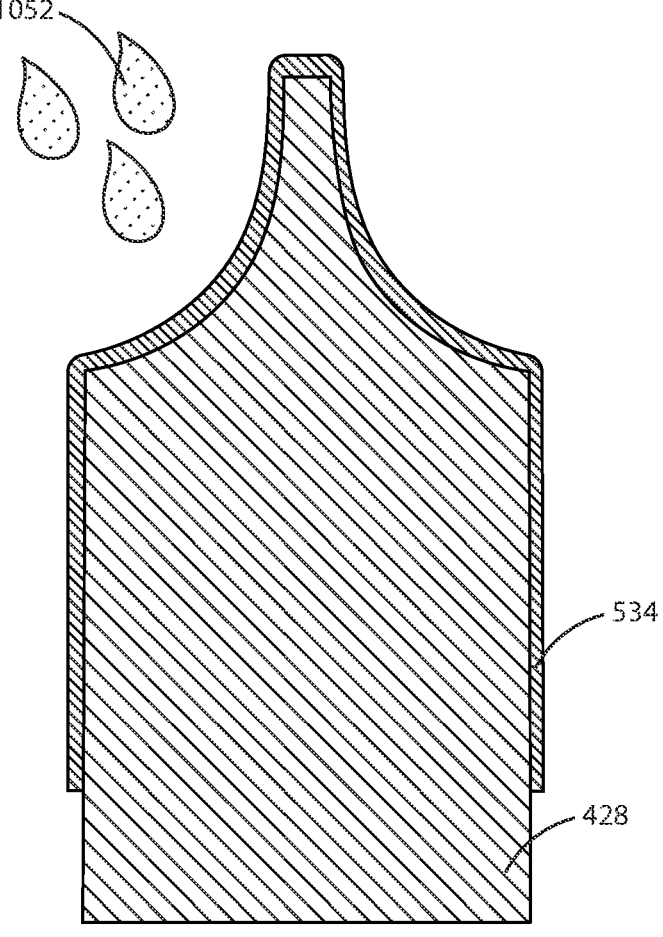
FIG. 10 is a cross-sectional view of tissue being cross-linked on a mold in accordance with various embodiments herein.
Figure 11:
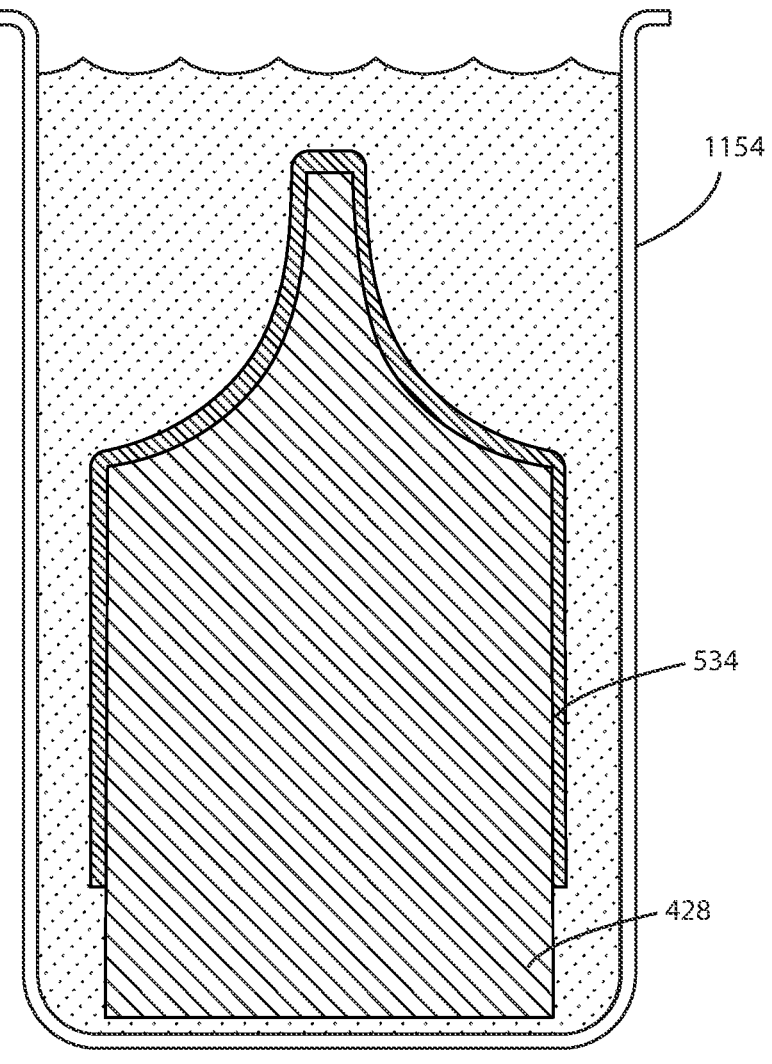
FIG. 11 is a cross-sectional view of tissue being cross-linked on a mold in accordance with various embodiments herein.

Referring now to FIGS. 10 and 11, cross-sectional views of tissue 534 being crosslinked on a mold 428 are shown in accordance with various embodiments herein. FIG. 10 shows a fixing solution 1052 being applied to the tissue 534. In some embodiments, the fixing solution 1052 can be sprayed onto the tissue 534 while the tissue 534 is on the mold 428. In other embodiments, such as shown in FIG. 11, the tissue 534 can be submerged in a tank or container 1154 of fixing solution 1052.

Cross-linking the tissue 534 can result in the tissue 534 maintaining its shape after the mold 428 is removed or separated from the tissue 534. In some embodiments, the degree of cross-linking is substantially uniform across all portions of the tissue 534. However, in some embodiments, the animal tissue 534 exhibits a different degree of cross-linking in different areas of the implantable heart valve 100 assembly. For example, in some embodiments, the portion of the tissue 534 forming the leaflets is more highly cross-linked than other areas such as the area forming the inner skirt and/or outer skirt. This can be performed in various ways. In some embodiments, the tissue while it is still on the mold can be dipped upside down with the leaflet end down into a fixing solution such that the area of the leaflets is submerged in the fixing solution, but the portion forming the inner skirt is not. In other embodiments, the tissue can be dipped into a fixing solution so that the inner skirt end is submerged into the fixing solution. Thus, in some embodiments, the area of a leaflets is more highly cross-linked than the inner skirt area to provide the leaflets with toughness. However, in some embodiments, the inner skirt area is more highly cross-linked than the area of the leaflets. In this manner, the degree of cross-linking in different areas of the valve can be optimized independently.

Figure 12:
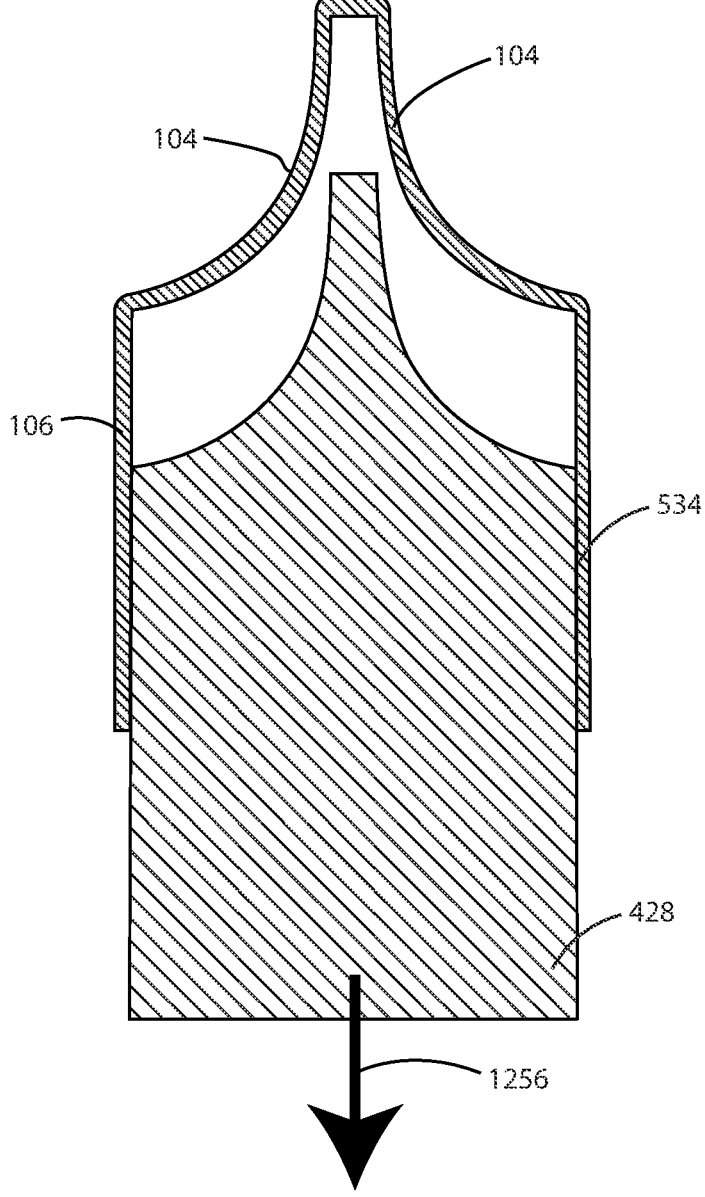
FIG. 12 is a cross-sectional view of a mold being removed from the tissue in accordance with various embodiments herein.

After the tissue 534 has been cross-linked on the mold 428, the mold 428 can be removed from the tissue 534 as shown in FIG. 12. FIG. 12 shows a cross-sectional view of a mold 428 being removed from the tissue 534 in accordance with various embodiments herein. The mold 428 can be separated from the tissue 534, such as by keeping the tissue 534 stationary and moving the mold in the direction of arrow 1256.

Figure 13:
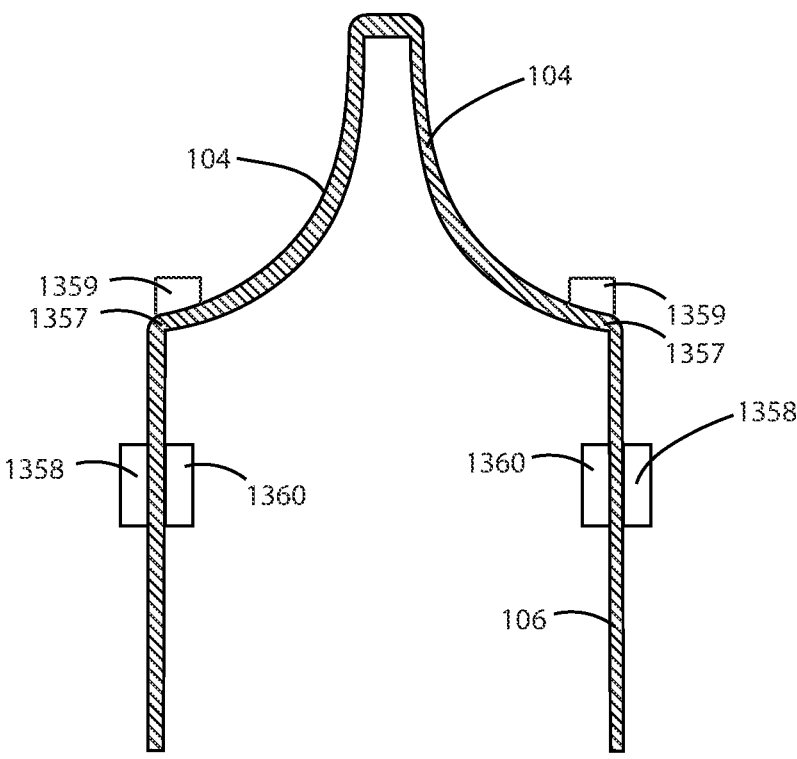
FIG. 13 is a cross-sectional view of a portion of the heart valve in accordance with various embodiments herein.

Referring now to FIG. 13, a cross-sectional view of a portion of the heart valve 100 is shown in accordance with various embodiments herein. The heart valve can include leaflets 104 and an inner skirt 106. In various embodiments, the plurality of leaflets 104 can exhibit a curved bias from the in-situ cross-linking, such as shown in FIG. 13.

In some embodiments, the heart valve can include one or more reinforcing structures, such as a reinforced portion of the tissue 534. The reinforcing structure(s) can be positioned at areas of high stress such as that caused by leaflet 104 movement or from sutures attaching the cross-linked tissue 534 to a frame 102. The reinforcing structures can include added animal tissue or a polymeric material, such that the heart valve can effectively be thicker at the locations of the reinforcing structures. In some embodiments, the reinforcing structures can include a polymeric mesh, such as a polyethylene terephthalate (PET) mesh. In some embodiments, the reinforcing structures can include one or more outer reinforcements 1358 and/or one or more inner reinforcements 1360.

In various embodiments, each of the plurality of valve leaflets 104 can include a commissure and a nadir 1357. The commissure can refer to the area of a leaflet 104 where it meets an adjacent leaflet 104 adjacent the circumference of the valve. The nadir 1357 can refer to the area of the leaflet 104 where it joins the inner skirt 106. In various embodiments, a reinforcement 1359 can be located at the nadir 1357 of a leaflet. In some embodiments, a reinforcement 1359 can be positioned in the area of at least one of the commissures and the nadir 1357.

It will be appreciated that animal derived tissue can have fibers (including, but not limited to collagen fibers) and/or other structures therein that exhibit a degree of directionality such that the tissue is more elastic in one direction than in another. In various embodiments herein, the directional properties of the tissue can be purposely aligned in certain directions with respect to the structure of the valve that is created.

Figure 14:
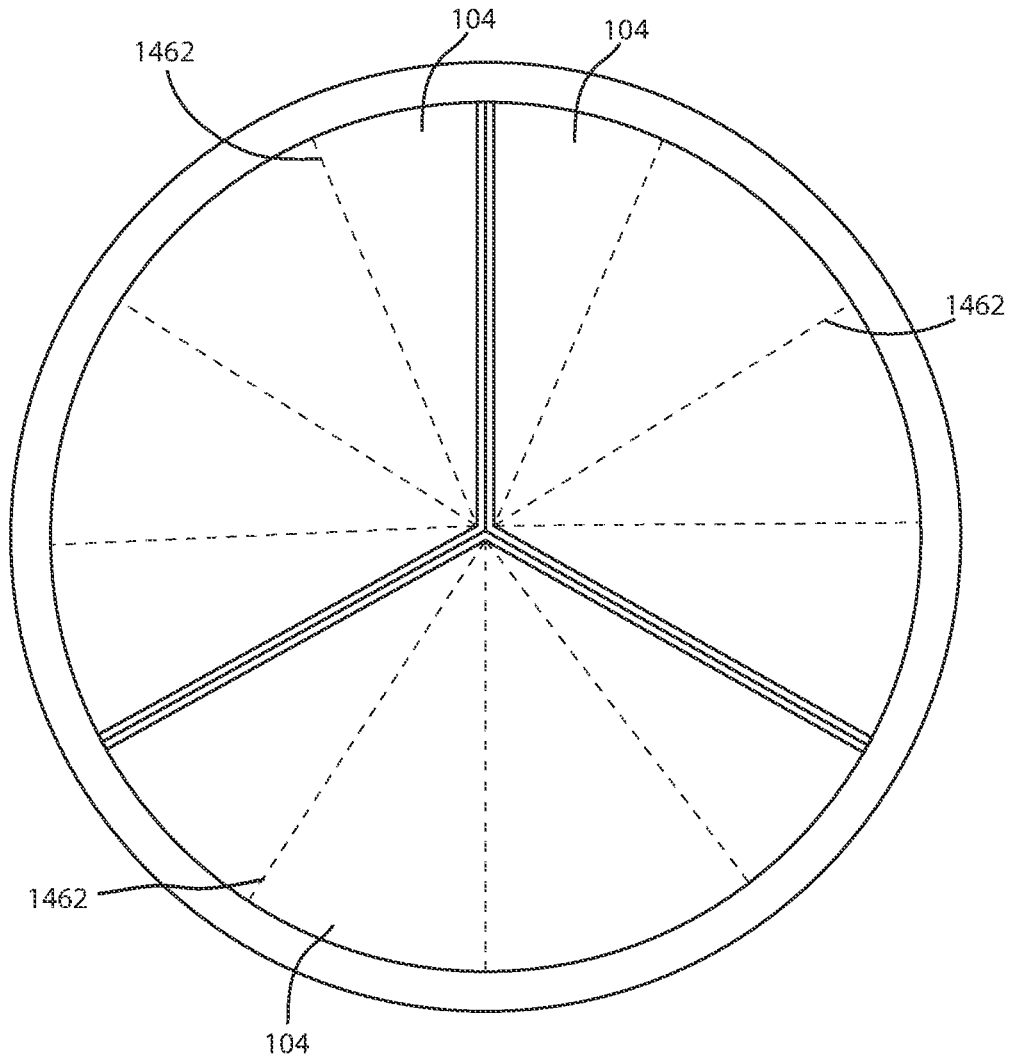
FIG. 14 is a schematic end view of a closed valve in accordance with various embodiments herein.
Figure 15:
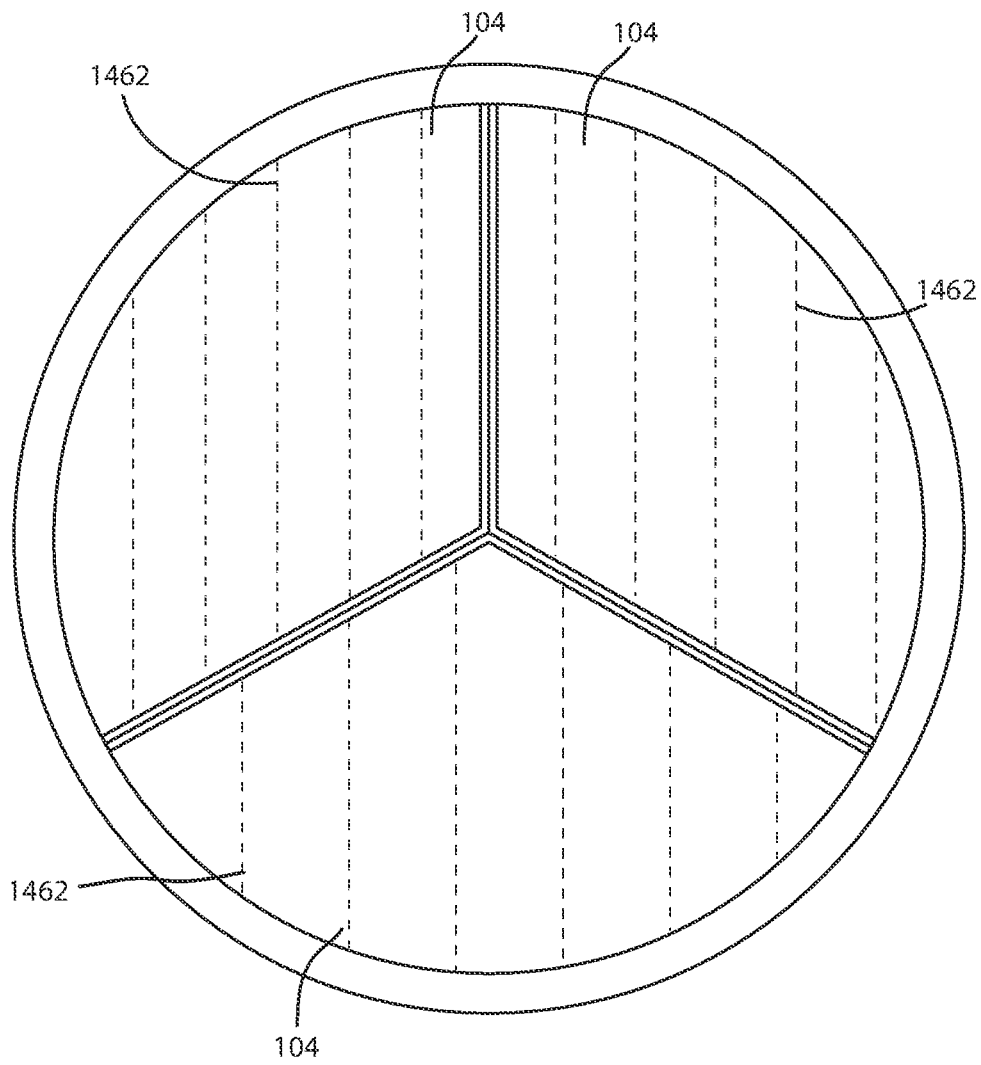
FIG. 15 is a schematic end view of a closed valve in accordance with various embodiments herein.
Figure 16:
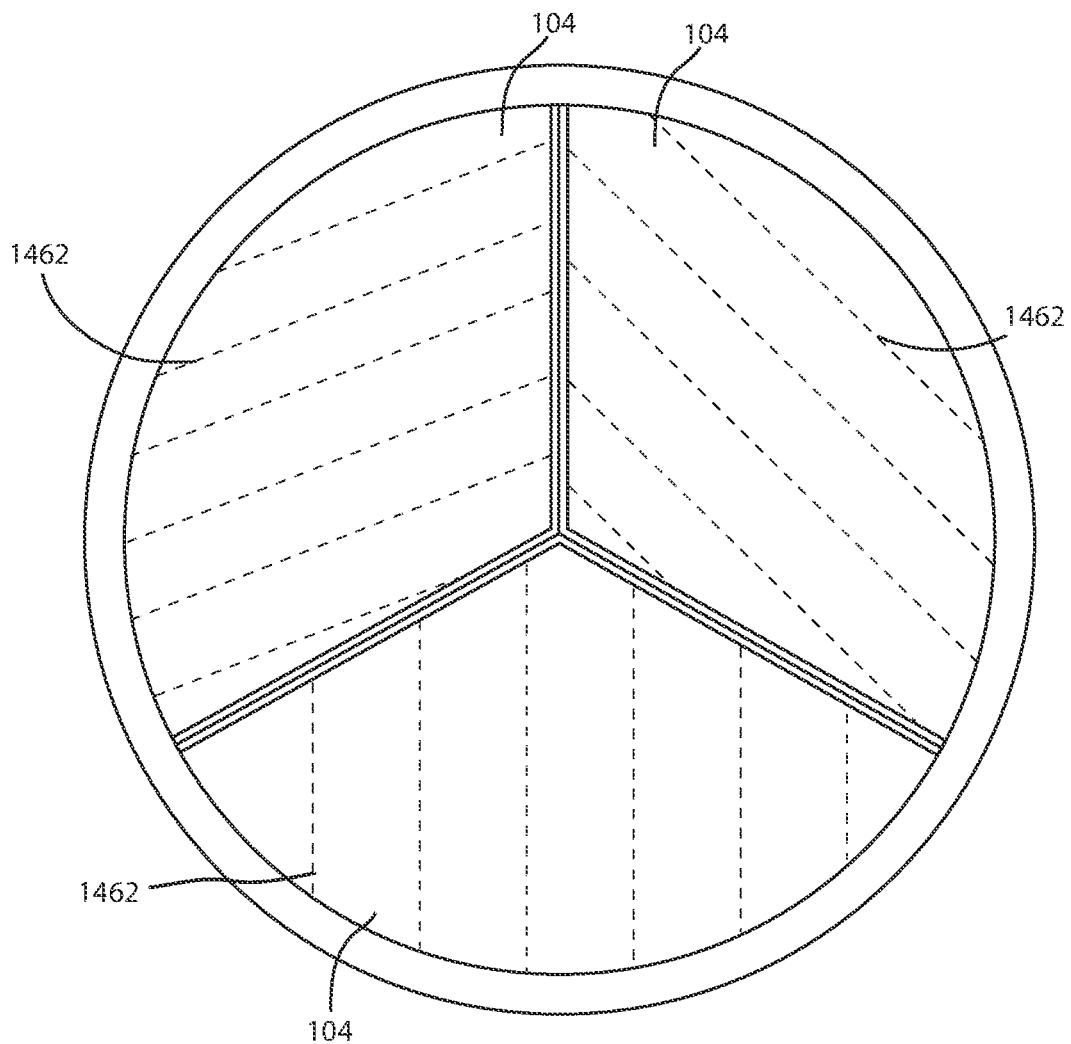
FIG. 16 is a schematic end view of a closed valve in accordance with various embodiments herein.

FIGS. 14-16 show various ways in which the natural fibers in the tissue, such as pericardial tissue, can be arranged in the valve 100. Referring now to FIG. 14, a schematic end view of a closed valve 100 is shown in accordance with various embodiments herein. The tissue of the leaflets 104 can include fibers 1462. The fibers 1462 can be aligned, such that the fibers exhibit a symmetric radial arrangement around the valve 100. A symmetric radial arrangement can provide a desirable symmetry of properties (such as symmetric flexural properties) for each leaflet.

However, in other embodiments, such as shown in FIGS. 15-16, the fibers 1462 of the valve leaflets 104 can exhibit an asymmetric arrangement.

Frame

The frame 102, or at least some components thereof, can be formed of various materials including, but not limited to, polymers, metals, metal alloys, ceramics, and composites. Exemplary materials can specifically include biocompatible materials. Exemplary materials can specifically include corrosion resistant metals and metal alloys. In some embodiments, the frame 102 can be at least partially formed of nitinol or NiTiCo. In some embodiments, the frame 102 can be at least partially formed of a cobalt-chromium alloy. In some embodiments, the frame 102 can be at least partially formed of platinum. In some embodiments, the frame 102 can be at least partially formed of a tantalum alloy. In some embodiments, the frame 102 can be at least partially formed of a stainless steel.

Tissue

The tissue used for the heart valves described herein can include a naturally derived tissue, such as an animal tissue. In various embodiments, bovine, porcine, ovine or caprine tissue can be used as the natural tissue. In some embodiments, the naturally derived tissue can specifically include pericardium tissue. However, other types of tissue can also be used such as kidney capsule tissue, small intestine submucosa tissue, cultured animal tissue, or the like.

In various embodiments, the animal tissue 534 has a thickness of 100 to 500 microns. In some embodiments, the thickness can be greater than or equal to 100 microns, 130 microns, 160 microns, 190 microns, 220 microns, or 250 microns. In some embodiments, the thickness can be less than or equal to 1000 microns, 850 microns, 700 microns, 550 microns, 400 microns, or 250 microns. In some embodiments, the thickness can fall within a range of 100 microns to 1000 microns, or 130 microns to 850 microns, or 160 microns to 700 microns, or 190 microns to 550 microns, or 220 microns to 400 microns.

In some embodiments, the thickness can be measured when the tissue is fresh (unfixed). In some embodiments, the thickness can be measured when the tissue is fixed (cross-linked).

Cross-linking of the tissue can be performed in various ways. In some embodiments, a homobifunctional crosslinking agent can be used. In some embodiments, a heterobifunctional crosslinking agent can be used. In some embodiments, a compound for crosslinking includes one or more of an amine-reactive group, a carboxyl-to-amine reactive group, a sulfhydryl-reactive group, an aldehyde-reactive group, a photo-reactive group, a hydroxyl reactive group, or an azide-reactive group. In some embodiments, cross-linking is performed by exposing the tissue to a glutaraldehyde solution. However, many other chemical compounds can be used to perform crosslinking.

Methods

Many different methods are contemplated herein, including, but not limited to, methods of making, methods of using, and the like. Aspects of system/device operation described elsewhere herein can be performed as operations of one or more methods in accordance with various embodiments herein.

Figure 17:
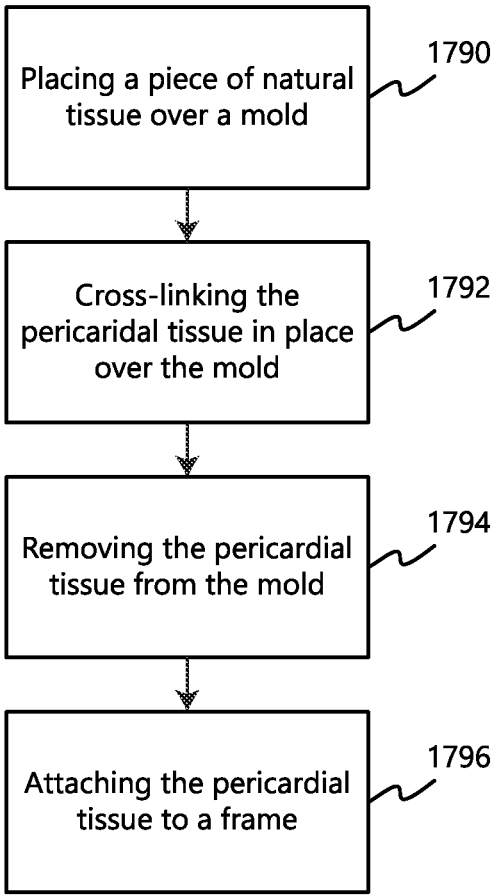
FIG. 17 is a schematic representing a method of making a heart valve in accordance with various embodiments herein.

FIG. 17 shows a flowchart depicting a method of making an implantable heart valve assembly. The method can include placing a piece of pericardial tissue over a mold 1790. The method can include cross-linking the pericardial tissue in place over the mold 1792. The method can include removing the pericardial tissue from the mold 1794. The method can further include attaching the pericardial tissue to a frame 1796. In some embodiments, the pericardial tissue forms a seamless junction between a plurality of valve leaflets and an inner skirt.

In some embodiments, the method can further include cutting the pericardial tissue to form valve leaflet edges.

In some embodiments, the method can further include the pericardial tissue in place on the mold.

In some embodiments, the method can further include wrapping an end of the pericardial tissue up and over an end of the frame to form an outer skirt.

In some embodiments, cross-linking is performed by exposing the tissue to a glutaraldehyde solution. In some embodiments, the method can further include holding the pericardial tissue on the mold using vacuum pressure. In some embodiments, the method can further include holding the pericardial tissue on the mold using fluid pressure. In some embodiments, the method can further include holding the pericardial tissue on the mold using mechanical tension. In some embodiments, the method can further include placing a piece of pericardial tissue over a mold further comprises rolling a sheet of pericardial tissue around the mold and forming a line of sutures longitudinally along the mold to hold the pericardial tissue in place. In some embodiments, the method can further include placing a piece of pericardial tissue over a mold further comprises placing a non-planar piece of fresh pericardial tissue over the mold.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An implantable heart valve assembly comprising:
   a plurality of valve leaflets, the plurality of valve leaflets comprising an animal tissue, wherein the animal tissue comprises pericardium tissue;
   a seamless inner skirt, the seamless inner skirt comprising the animal tissue; and
   a metal frame;
   wherein the plurality of valve leaflets and the seamless inner skirt are formed of a continuous piece of animal tissue.

2. The implantable heart valve assembly of claim 1, wherein the leaflets and seamless inner skirt are attached without suturing.

3. The implantable heart valve assembly of claim 1, wherein a first surface of the animal tissue defines an outer portion of the seamless inner skirt and an outer portion of the plurality of valve leaflets.

4. The implantable heart valve assembly of claim 1, further comprising:
   an outer skirt, the outer skirt comprising an animal tissue.

5. An implantable heart valve assembly comprising:
   a plurality of valve leaflets, the plurality of valve leaflets comprising an animal tissue;
   a seamless inner skirt, the seamless inner skirt comprising the animal tissue; and
   a metal frame;
   wherein the plurality of valve leaflets and the seamless inner skirt are formed of a continuous piece of animal tissue;
   wherein a first surface of the animal tissue defines an outer portion of the seamless inner skirt and an outer portion of the plurality of valve leaflets;
   wherein the plurality of valve leaflets exhibits a symmetric pericardial fiber orientation.

6. The implantable heart valve assembly of claim 5, wherein the animal tissue has a thickness of 100 to 500 microns.

7. The implantable heart valve assembly of claim 5, wherein the animal tissue exhibits a different degree of cross-linking in different areas of the implantable heart valve assembly.

8. The implantable heart valve assembly of claim 5, further comprising:
   an outer skirt, the outer skirt comprising an animal tissue.

9. The implantable heart valve assembly of claim 8, wherein the plurality of valve leaflets, the seamless inner skirt, and the outer skirt are formed of the continuous piece of animal tissue.

10. The implantable heart valve assembly of claim 8, wherein the plurality of valve leaflets, the seamless inner skirt, and the outer skirt are formed of a single piece of pericardium.

11. The implantable heart valve assembly of claim 8, wherein the outer skirt wraps around an end of the metal frame and rests against an outside surface of the metal frame.

12. The implantable heart valve assembly of claim 5, wherein the plurality of valve leaflets and the seamless inner skirt are sutured to the metal frame.

13. The implantable heart valve assembly of claim 5, wherein the plurality of valve leaflets comprising:
   commissures;
   a nadir; and
   a reinforcing structure, wherein the reinforcing structure is positioned in the area of at least one of the commissures and the nadir.

14. The implantable heart valve assembly of claim 5, wherein the plurality of valve leaflets exhibits a curved bias from in situ cross-linking.

15. The implantable heart valve assembly of claim 5, wherein the leaflets and seamless inner skirt are attached without suturing.

16. An implantable heart valve assembly comprising:
   a plurality of valve leaflets, the plurality of valve leaflets comprising an animal tissue;
   a seamless inner skirt, the seamless inner skirt comprising the animal tissue; and
   a metal frame;
   wherein the plurality of valve leaflets and the seamless inner skirt are formed of a continuous piece of animal tissue;
   wherein a first surface of the animal tissue defines an outer portion of the seamless inner skirt and an outer portion of the plurality of valve leaflets;
   wherein the plurality of valve leaflets exhibits an asymmetric pericardial fiber orientation.

17. The implantable heart valve assembly of claim 16, wherein the animal tissue has a thickness of 100 to 500 microns.

18. The implantable heart valve assembly of claim 16, wherein the animal tissue exhibits a different degree of cross-linking in different areas of the implantable heart valve assembly.

19. The implantable heart valve assembly of claim 16, further comprising:
   an outer skirt, the outer skirt comprising an animal tissue.

20. The implantable heart valve assembly of claim 19, wherein the plurality of valve leaflets, the seamless inner skirt, and the outer skirt are formed of the continuous piece of animal tissue.

* * * * *